(12) United States Patent
Gavriely et al.

(10) Patent No.: US 10,194,916 B2
(45) Date of Patent: Feb. 5, 2019

(54) APPLICATOR DEVICE AND METHOD OF USE FOR EXSANGUINATION TOURNIQUET

(71) Applicant: OHK MEDICAL DEVICES, LTD., Haifa (IL)

(72) Inventors: Noam Gavriely, Haifa (IL); Oded Fishelzon, Haifa (IL)

(73) Assignee: OHK MEDICAL DEVICES, LTD., Haifa (IL)

( * ) Notice: Subject to any disclaimer, the term of this patent is extended or adjusted under 35 U.S.C. 154(b) by 529 days.

(21) Appl. No.: 14/902,421

(22) PCT Filed: Jul. 2, 2013

(86) PCT No.: PCT/IL2013/050563
§ 371 (c)(1),
(2) Date: Dec. 31, 2015

(87) PCT Pub. No.: WO2015/001542
PCT Pub. Date: Jan. 8, 2015

(65) Prior Publication Data
US 2016/0143647 A1     May 26, 2016

(51) Int. Cl.
*A61B 17/132*     (2006.01)
(52) U.S. Cl.
CPC ................ *A61B 17/1322* (2013.01)
(58) Field of Classification Search
CPC .............. A61B 17/1322; A61B 17/132; A61B 17/1325; A61B 17/1327; A61B 17/135; A61B 17/1355
See application file for complete search history.

(56) References Cited

U.S. PATENT DOCUMENTS 5,304,202 A * 4/1994 Stahl .................. A61B 17/1322
606/201
5,344,389 A     9/1994 Walsdorf
2003/0153936 A1     8/2003 El-Galley
(Continued)

FOREIGN PATENT DOCUMENTS

DE     365452     6/1924
EP     0623326     11/1994

OTHER PUBLICATIONS

International Search Report for PCT/IL2013/050563 dated Oct. 16, 2013.
(Continued)

*Primary Examiner* — Wade Miles
(74) *Attorney, Agent, or Firm* — Heslin Rothenberg Farley & Mesiti P.C.; Jacquelyn A. Graff

(57) ABSTRACT

An applicator device, system and method for use with an exsanguination tourniquet are disclosed. The applicator device includes a body with a proximal end and a distal end, a first opening at the proximal end, and a conduit connecting the proximal end and the distal end. The system includes the applicator device and an exsanguination device. The method of applying an exsanguination tourniquet over a patient's limb, includes selecting an applicator device and correspondingly sized exsanguination tourniquet, placing the exsanguination tourniquet over the applicator device, placing the applicator device over the patient's limb, and rolling the exsanguination tourniquet over the applicator device and a portion of the patient's limb from the distal end of the limb.

17 Claims, 9 Drawing Sheets

(56) References Cited

U.S. PATENT DOCUMENTS

| | | |
|---|---|---|
| 2005/0080450 A1 | 4/2005 | Gavriely |
| 2005/0261734 A1* | 11/2005 | Sakura .............. A61B 17/1322 606/201 |
| 2007/0119882 A1 | 5/2007 | Scott |
| 2009/0209891 A1* | 8/2009 | Gavriely ............. A61B 17/132 601/134 |
| 2009/0254012 A1* | 10/2009 | Gavriely ............. A61B 17/132 601/134 |
| 2010/0121245 A1 | 5/2010 | Marino |
| 2010/0270341 A1 | 10/2010 | Joosten |

OTHER PUBLICATIONS

Written Opinion of the International Searching Authority for PCT/IL2013/050563 dated Oct. 16, 2013.

European Search Report for corresponding European Application 13888877.1 dated Jun. 16, 2017.

\* cited by examiner

APPLICATOR DEVICE AND METHOD OF USE FOR EXSANGUINATION TOURNIQUET

CROSS REFERENCE TO RELATED APPLICATION

This application is a national stage filing under section 371 of International Application No. PCT/IL2013/050563, filed on Jul. 2, 2013, and published in English on Jan. 8, 2015 as WO 2015/001542 A1, the entire contents of which is being hereby incorporated herein by reference.

FIELD OF THE INVENTION

The present invention relates generally to the preparation of the limb for surgery. More specifically, but not exclusively, the present invention concerns an applicator device and method for use with an exsanguination tourniquet for the management of blood flow into a limb during surgery.

BACKGROUND OF THE INVENTION

Creation of a blood free surgical field during orthopedic, vascular and plastic surgery has been the standard of care for over 100 years. The initial device was described by Friederich August von Esmarch in 1873 and is still being used today as the Esmarch bandage. In 1908, Dr. Harvey Cushing first described the use of a pneumatic tourniquet to occlude the blood flow into the scalp during brain surgery. Combination of an Esmarch bandage for squeezing the blood away from a limb (exsanguination) and a pneumatic tourniquet to occlude arterial blood flow is currently used in over 90% of limb operations. The use of a pneumatic tourniquet to occlude the arterial blood flow into a limb is associated with a number of side effects and adverse reactions. The side effects and adverse reactions may include tourniquet paralysis, which is transient or permanent nerve damage caused by the mechanical affect of the wide tourniquet cuff on the nerve. (Ochoa at el. Anatomical changes in peripheral nerves compressed by a pneumatic tourniquet. J Anat. 1972; 113(Pt 3):433-55.) In addition, side effects and adverse reactions may include skin lesions, which are skin abrasions or liquid blisters at the site of tourniquet placements (tourniquet burn) and tourniquet pain, which is tenderness at the site where the tourniquet was placed, that may last for days or even weeks.

More recently devices combining the exsanguination effect of the Esmarch and the blood flow blocking of a tourniquet are being used. These exsanguination tourniquet devices may be difficult to use when a patient is under anesthesia resulting in a patient's finger or toe being improperly inserted into the exsanguination tourniquet. The misplacement of a finger or toe occasionally leads to loss of operating room time and frustration of the surgical team. The present invention overcomes the shortcomings of the prior art and others.

SUMMARY OF THE INVENTION

Aspects of the present invention provide an applicator device, system, and method for enhancing the safety and ease of applying an exsanguination tourniquet over a patient's hand or foot.

In one aspect, provided herein is an applicator device including a body with a proximal end and a distal end, a first opening at the proximal end, and a conduit connecting the proximal end and the distal end.

In another aspect, provided herein is a system including an applicator device and an exsanguination tourniquet. The applicator device includes a body with a first end and a second end. The first end includes a first opening. The applicator device also includes a conduit connecting the first end to the second end.

In yet another aspect, provided herein is a method of applying an exsanguination tourniquet over a patient's limb, including selecting an applicator device and correspondingly sized exsanguination tourniquet. The method also includes placing the exsanguination tourniquet over the applicator device and placing the applicator device over the patient's limb. The method further includes rolling the exsanguination tourniquet over the applicator device and a portion of the patient's limb from the distal end of the limb.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION FOR CARRYING OUT THE INVENTION

Generally stated, disclosed herein is an applicator device for applying an exsanguination tourniquet to a patient's limb. Further, a system and methods for applying an exsanguination tourniquet to a patient's limb using the applicator device are shown.

In this detailed description and the following claims, the words proximal, distal, anterior, posterior, medial, lateral, superior and inferior are defined by their standard usage for indicating a particular part of a bone or device according to the relative disposition of the natural bone or directional terms of reference. For example, "proximal" means the portion of a device nearest the torso, while "distal" indicates the portion of the device farthest from the torso. As for directional terms, "anterior" is a direction towards the front side of the body, "posterior" means a direction towards the back side of the body, "medial" means a direction towards the midline of the body, "lateral" is a direction towards the sides or away from the midline of the body, "superior" means a direction above and "inferior" means a direction below another object or structure.

Figure 1:
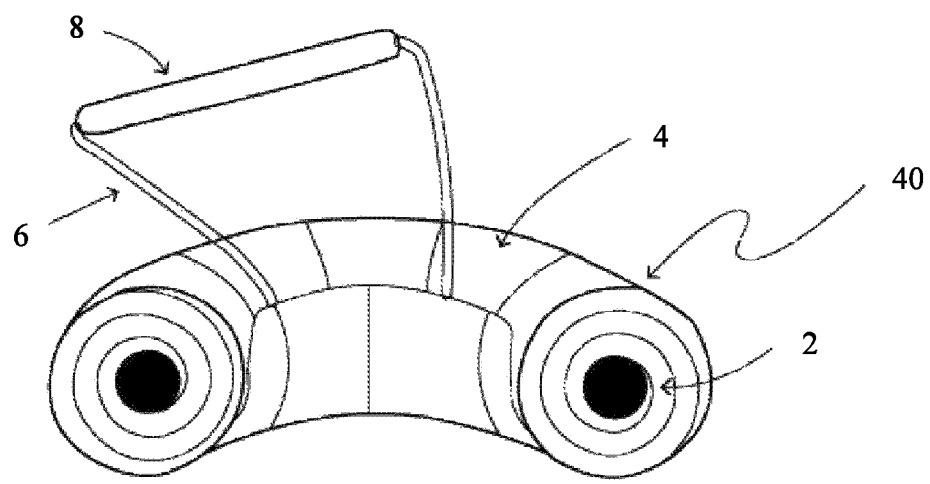
FIG. 1 is a cross section of a prior art exsanguination tourniquet.

FIG. 1 shows a cross section of a prior art exsanguination tourniquet 40. The exsanguination tourniquet 40 issued as U.S. Pat. No. 7,854,748 which is herein incorporated by reference in its entirety. The other half of the exsanguination tourniquet 40 may be generally symmetrical to the portion shown in FIG. 1. The exsanguination tourniquet 40 may be constructed from an elastomeric ring 2 and may include an elastic sleeve 4 coupled to a plurality of straps 6 wrapped around the elastomeric ring 2. The straps 6 may include at least one handle 8.

Figure 2:
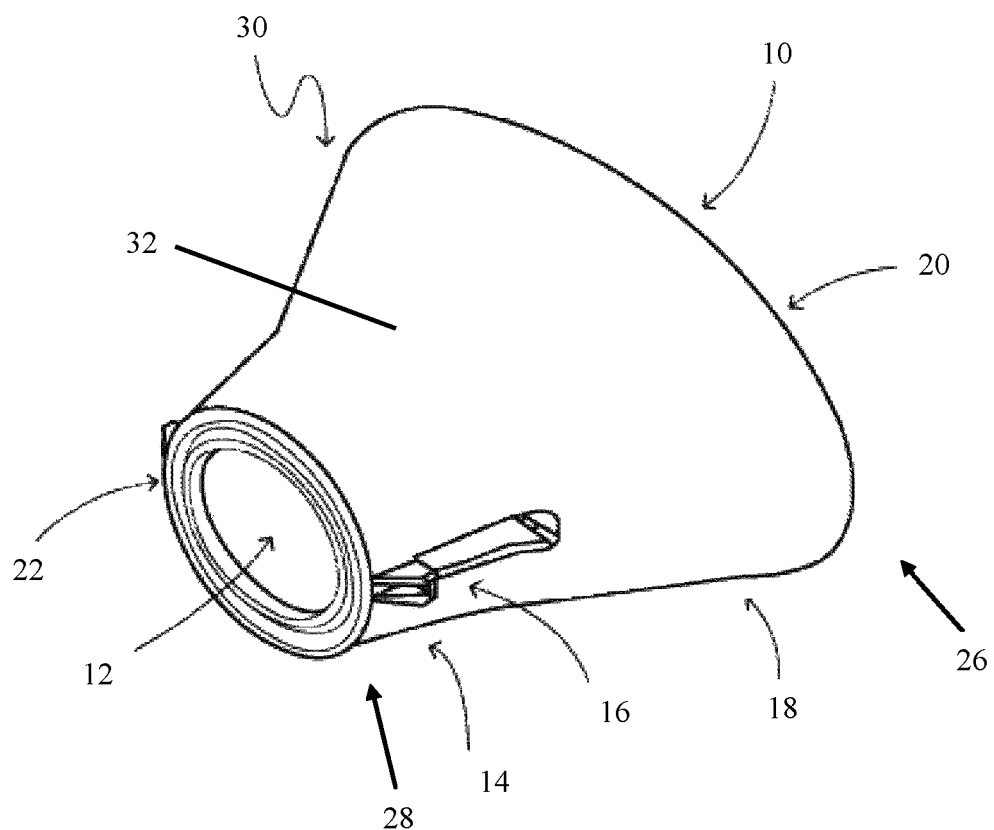
FIG. 2 is an isometric view of an applicator device, in accordance with an aspect of the present invention.
Figure 3:
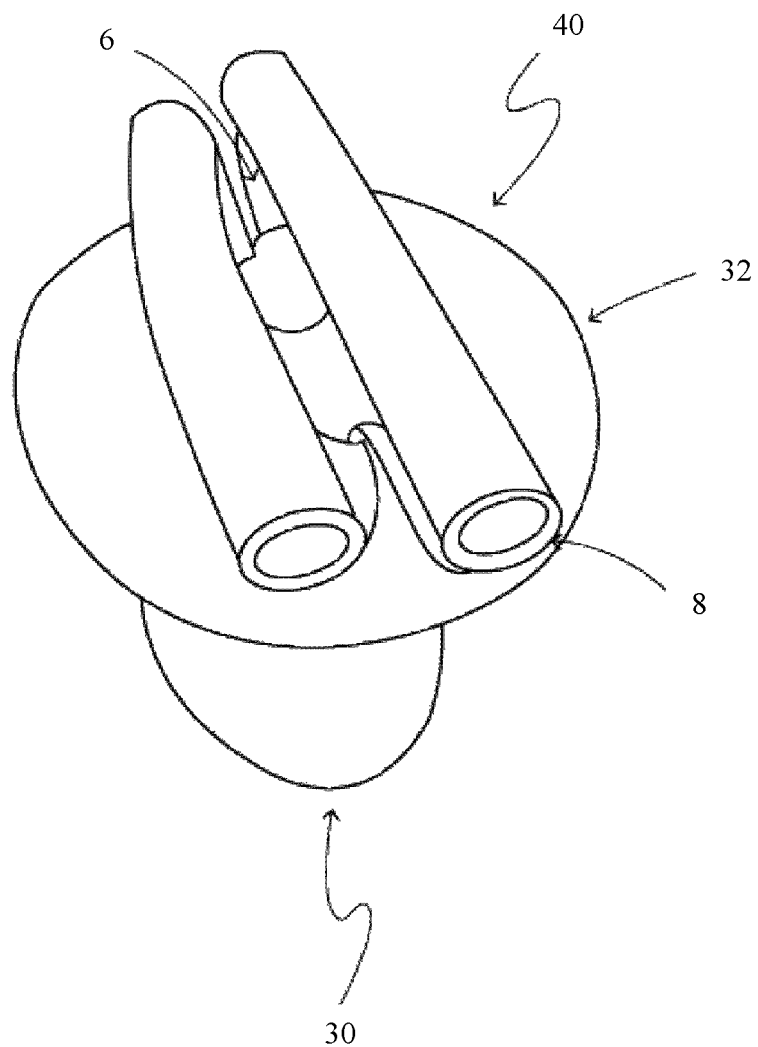
FIG. 3 is an isometric view of an exsanguination tourniquet mounted on the applicator device of FIG. 2, in accordance with an aspect of the present invention.
Figure 4:
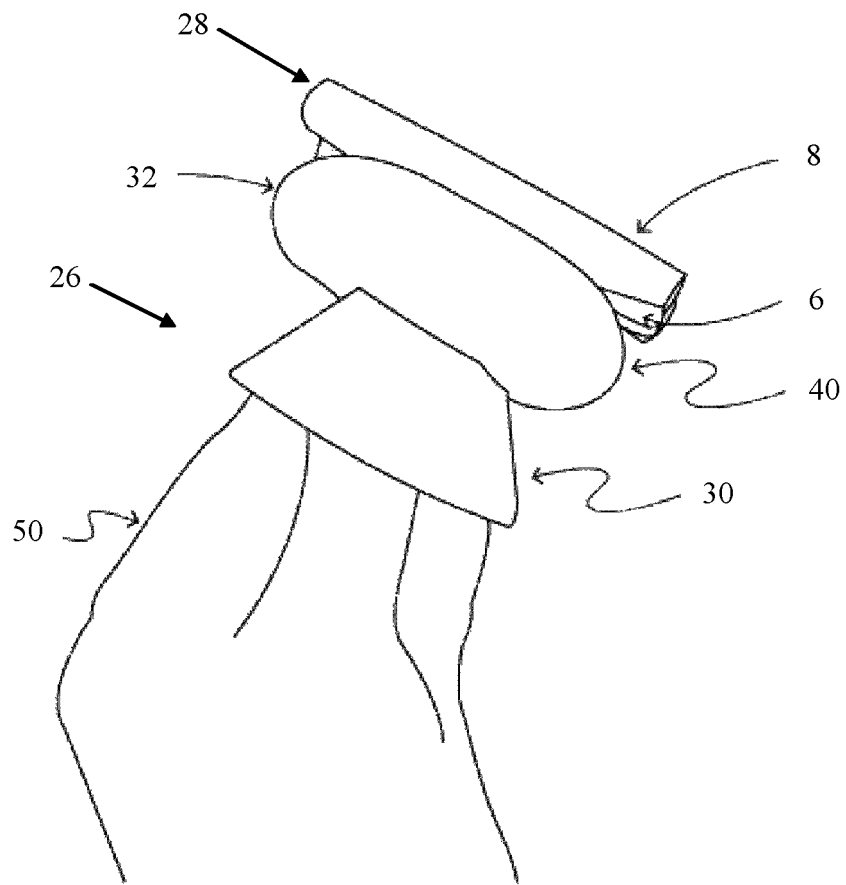
FIG. 4 is an isometric view of the exsanguination tourniquet and applicator device of FIG. 3 placed on the fingers of a patient, in accordance with an aspect of the present invention.
Figure 5:
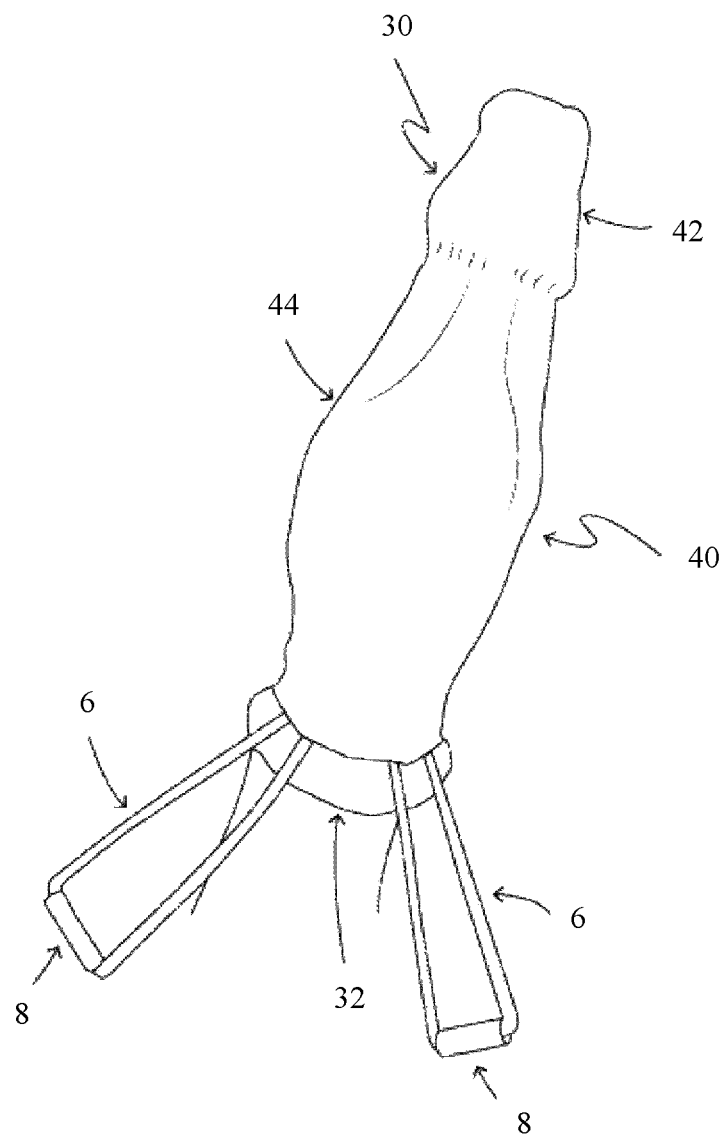
FIG. 5 is an isometric view of the exsanguination tourniquet and applicator device of FIG. 3 in a deployed position, in accordance with an aspect of the present invention.
Figure 6:
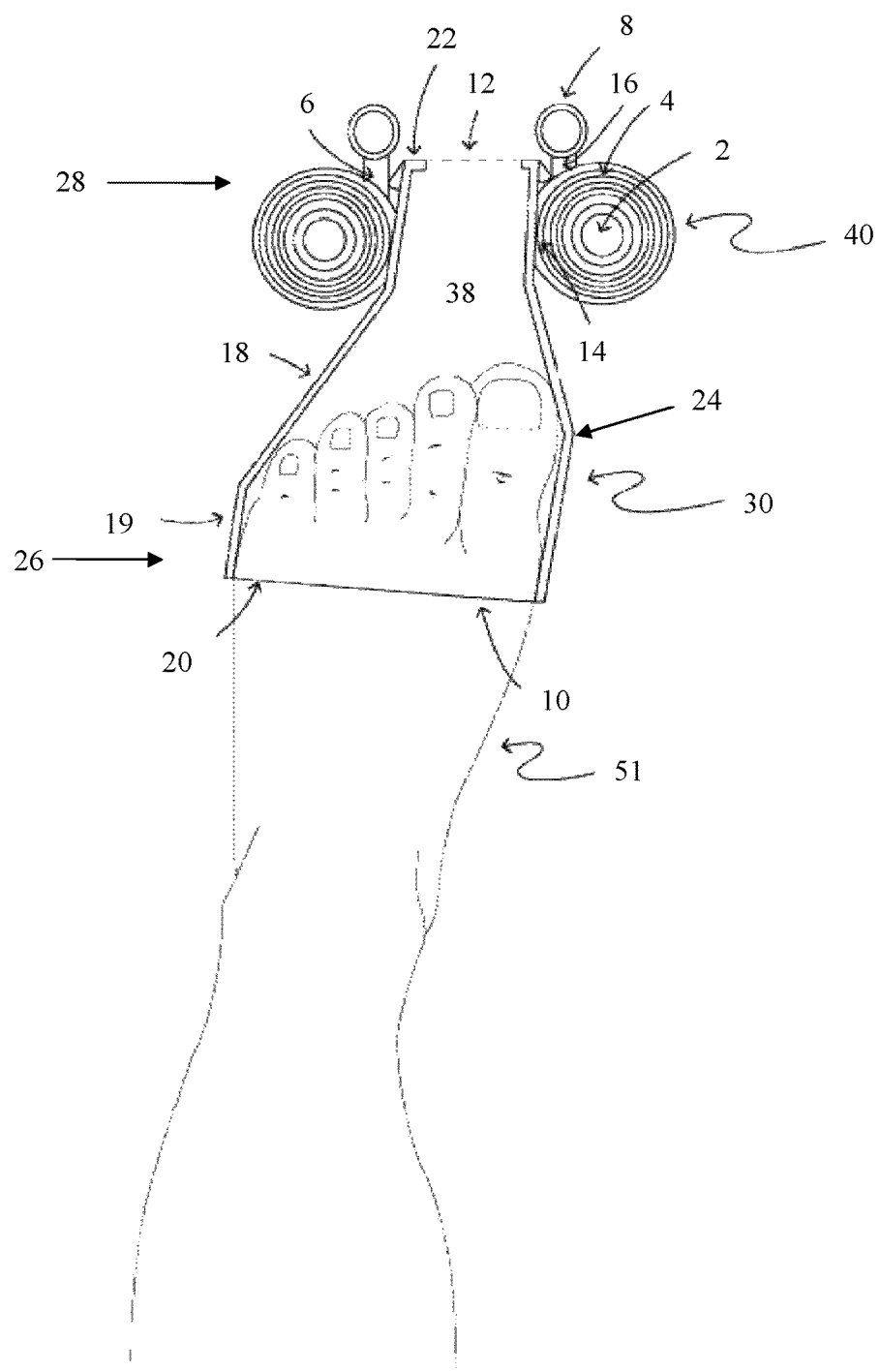
FIG. 6 is a top view of a patient's foot with a cross section of the exsanguination tourniquet of FIG. 3 with the applicator device of FIG. 2 placed on the toes of the patient, in accordance with an aspect of the present invention.

Referring to the drawings, wherein like reference numerals are used to indicate like or analogous components throughout the several views, and with particular reference to FIGS. 2-7, there is illustrated an exemplary embodiment applicator device or accessory 30. In one embodiment, as shown in FIGS. 2-3, the applicator device 30 may be used with the exsanguination tourniquet 40. The applicator device 30 may substantially enhance the safety and ease of applying the exsanguination tourniquet 40 over a patient's fingers or toes. The applicator device 30 may also be used with the exsanguination tourniquet 40 to overcome potential difficulties of the exsanguination tourniquet 40 including, but not limited to, collecting all the fingers or toes inside the exsanguination tourniquet 40 and initiating the exsanguination tourniquet 40 to roll over the hand or the foot of the patient. The applicator device 30 enables all of the patient's fingers or toes to be gathered together into a guiding cone 24, as seen in FIG. 6, and provides for a gradual expansion for the application of the exsanguination tourniquet 40.

In one embodiment, FIGS. 2-7 show an applicator device 30 for use with the exsanguination tourniquet 40. FIG. 2 shows the applicator device 30 which may include a body 32 with a proximal or first end 26 having a first opening 10 and a distal or second end 28 which may have a second opening 12. Alternatively, in an embodiment, the second end 28 may be closed. The first opening 10 may be, for example, generally oval shaped and generally wider than the second opening 12. The second opening 12 may be, for example, a generally circular opening and may be narrower than the first opening 10. The first opening 10 and the second opening 12 may be connected by a conduit 38, as seen in FIG. 6. The conduit 38 may be, for example, non-uniform or uniform. The conduit 38 may be constructed from, for example, a first or stem portion 14, which may be nearly cylindrical, an intermediate portion 18, which may an expanding member, and an engagement portion 19 for receiving a portion of the patient's limb. The first portion 14 may be equipped with plurality of protrusions 16. In addition, the stem portion 14 may be made of, for example, a non-flexible rigid material configured to withstand the force exerted by the exsanguination tourniquet 40 as it is applied to a patient's limb. The stem portion 14 is configured to reinforce the second opening 12 for supporting the exsanguination tourniquet 40. The engagement portion 19 may have a rounded profile to prevent injury to the patient's limb. In another embodiment the engagement portion 19 may be extended by a parallel walled oval cylinder (not shown). The engagement portion 19 and intermediate portion 18 may be configured to create a guiding cone 24 for a patient's fingers or toes. The second opening 12 may also include a rim 22. The rim 22 of the second opening 12 may be various sizes, including a wider rim 22 to reinforce the stem portion 14 and prevent it from collapsing under the radial pressure of the elastic exsanguination tourniquet 40 that is mounted over it, as shown in FIG. 3. In addition, the rim 22 may be configured to entirely cover the second opening 12.

FIGS. 3-5 show the application of the exsanguination tourniquet 40 onto the applicator device 30. As shown in FIG. 3, the torus or donut-shape of the elastic exsanguination tourniquet 40, with the handles 8 and straps 6, is mounted on the applicator device 30 prior to insertion over a patient's limb. The applicator device 30 coupled to the exsanguination tourniquet 40 may then be positioned over the patient's limb, for example, the patient's fingers 50 as shown in FIG. 4. The exsanguination tourniquet 40 may then be unrolled onto the patient's limb by pulling the handles 8 and the straps 6 of the exsanguination tourniquet 40. For example, as shown in FIG. 5, the exsanguination tourniquet 40 and the applicator device 30 are inserted over the hand and wrist of the upper extremity (not shown) of the patient. Once the exsanguination tourniquet 40 is unrolled onto the patient's limb, the sleeves 42 and 44 of the exsanguination tourniquet 40 cover both the applicator device 30 and the patient's limb respectively. The sleeves 42, 44 may be elastic and tight to the patient's limb.

FIG. 6 shows the applicator device 30 and the exsanguination tourniquet 40 combined into a unit that is aligned on a patient's foot 51. The patient's toes and the distal part of the foot 51 are inserted into the first opening 10 of the applicator device 30 while the exsanguination tourniquet 40 is coupled to the first portion 14 of the applicator device 30 and secured in place by the protrusions 16. The edge 20 of the first opening 10 of the applicator device 30 may be rounded and configured to avoid injury to the patient's skin. In the embodiment shown in FIG. 6, the extended first opening 10 may have a parallel-walled oval cylindrical conduit. The rim 22 of the second opening 12 of the applicator device 30 is reinforced to prevent it from gradually collapsing from the force exerted by the elastic exsanguination tourniquet 40. FIG. 6 shows the elastic inner core 2 of the exsanguination tourniquet 40 wrapped around by the sleeve 4 and the straps 6 connected to the handles 8. The engagement portion 19 of the applicator device 30 may also be tapered less than the intermediate portion 18 of the applicator device 30 and in one embodiment can have its walls parallel to each other. In another embodiment, the aspect of the applicator device 30 that faces the lateral part of the foot 51 may be shorter than the aspect of the engagement portion 19 that faces the medial aspect of the foot 51. In this embodiment the line connecting the intermediate portion 18 of the applicator device 30 and its straight engagement portion 19 is diagonal. Yet in another feature of this embodiment, the angle of the intermediate portion 18 of the conical part of the applicator device 30 is the same on both the lateral and medial aspects of the foot 51. In yet another embodiment, the intermediate portion 18 may be unequal medially and laterally.

Figure 7:
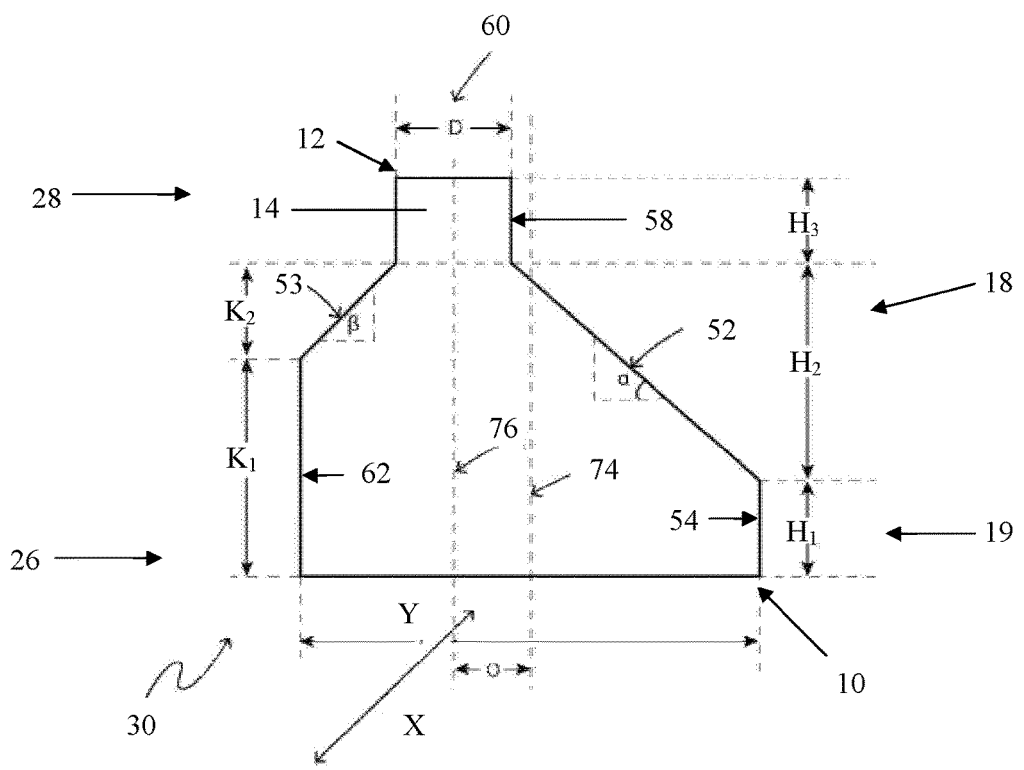
FIG. 7 is a schematic side elevational view of the applicator device of FIG. 2, in accordance with an aspect of the present invention.

As shown in FIG. 7, the applicator device 30 may include a center line 76 of the second end 28 offset relative to a center line 74 of the wide portion of the first end 26. The center line 76 may bisect the midpoint of the diameter D of the second end 28. The center line 74 may bisect the midpoint of a longitudinal axis of the first end 26. In one embodiment, this offset is medial so that the second opening 12 is closer to the big toe. The applicator device 30 is shown in FIG. 7, for example, in a right foot orientation. The medial offset places the second end 28 and the exsanguination tourniquet 40 directly in line with a firm and stable mechanical axis of the foot 51. In another embodiment, the offset is towards the lateral aspect of the foot 51, and yet in another embodiment, the second end 28 is directly in line with the center line 74 of the wide portion of the first opening 10 of the applicator device 30. The first opening 10 may include a width Y, which may extend along a longitudinal axis of the first opening 10, and a depth X, which may extend along a lateral axis of the first opening 10. The features of the applicator device 30 may also include angulated walls of the intermediate portion 18 of the applicator device 30 at an angle α for the first side wall 52 and an angle β for the second side wall 53 which is opposite the first side wall 52. It should be obvious to one skilled in the art that the angles vary in a continual way as the wall curves down and up to form the dorsal and plantar aspect of the applicator device 30 covering the hand 50 or the foot 51, as seen in FIGS. 4 and 6, respectively. In one embodiment, the angle α and the angle β are equal to each other in order to facilitate an even slope while rolling the exsanguination tourniquet 40 over the applicator device 30. Yet, in another embodiment, the angle α and the angle β are different. The angle α may range, for example, between approximately 45° and 75° and the angle β may range, for example, between approximately 45° and 75°. The angles α and β of the applicator device 30 are selected to enable the exsanguination tourniquet 40 to roll over the applicator device 30.

The applicator device 30, as shown in FIG. 7, may also include semi-parallel walls 54 and 62 of the engagement portion 19. The first wall 54 may have a height H1 and the second wall 62 may have a height K1. In the embodiment of the applicator device 30, such as shown in FIG. 2 and typically used for the upper extremity, H1 may equal K1 and they may range, for example, from zero to very small, such as, for example, less than 20 mm. In yet another embodiment, K1 may be different than H1, for example, K1 may be greater than H1. Some example ranges of the heights for H1 and K1 are shown in Table 1 below. The top side 60 of the second opening 12 may include a diameter D. The second opening 12 may be offset to be closer to the second wall 62 and the offset distance O may, for example, range between approximately 0 mm and 60 mm. The offset O may be between the center line 74 of the first opening 10 of the applicator device 30 and the center line 76 of the second opening 12 of the applicator device 30. It should be noted that the second opening 12 may be facing the center of the depth X along the lateral axis of the first opening 10 of the applicator device 30. The height of the first portion 14 of the applicator device 30 is H3 and is designed to provide a secure hold of the exsanguination tourniquet 40 (not shown in FIG. 7). The total height (H1+H2+H3) of the applicator device 30 minus the height H1 of the first wall 54 and the height H3 of the first portion 14 on one side of the applicator device 30, gives the height of H2 of the first side wall 52 of the applicator device 30. Likewise, the total height (K1+K2+H3) of the applicator device 30, minus the height K1 of the second wall 62 and the height H3 of the first portion 14 on the other aspect of the applicator device 30, provides the height K2 of the second side wall 53 of the applicator device 30 on the opposite side.

Table 1, for example, provides ranges of the approximate values of the parameters outlined above for the applicator device 30 for use on patient's with varying size hands and feet, for example, the patient's may range from having very small pediatric sized hands and feet to very large adult hands and feet, for example a shoe size of approximately 17 US/55 EU, although larger sizes are also contemplated.

TABLE 1

| Parameter | Foot | | Hand | |
|---|---|---|---|---|
| | Adult (mm) | Child (mm) | Adult (mm) | Child (mm) |
| X | 40-65 | 25-50 | 30-70 | 15-40 |
| Y | 80-120 | 60-100 | 50-80 | 30-70 |
| H1 | 0-60 | 0-40 | 0-40 | 0-25 |
| H2 | 40-90 | 25-50 | 20-50 | 15-40 |
| H3 | 20-50 | 10-40 | 10-35 | 10-30 |
| O | 0-40 | 0-30 | 0-10 | 0-10 |
| D | 20-50 | 20-40 | 20-40 | 20-30 |
| K1 | 0-60 | 0-40 | 0-40 | 0-25 |
| K2 | 40-90 | 25-50 | 20-50 | 15-40 |

As blood cannot be completely removed from the portions of the limb that are covered by the applicator device 30, the height (H1+H2/K1+K2) of the portion of the applicator device 30 that covers the patient's limb is minimized in one embodiment. By minimizing the height (H1+H2/K1+K2) more blood is able to be removed from the patient's foot or hand while still retaining the patient's fingers and toes in the applicator device 30 during application of the exsanguination tourniquet 40. In addition, the intermediate portion 18 and engagement portion 19 of the applicator device 30 which cover the distal part of a patient's hand or foot may be made of, for example, a semi-rigid or flexible material in order to facilitate at least partial blood removal from the covered portions of the patient's hand or foot.

Figure 8:
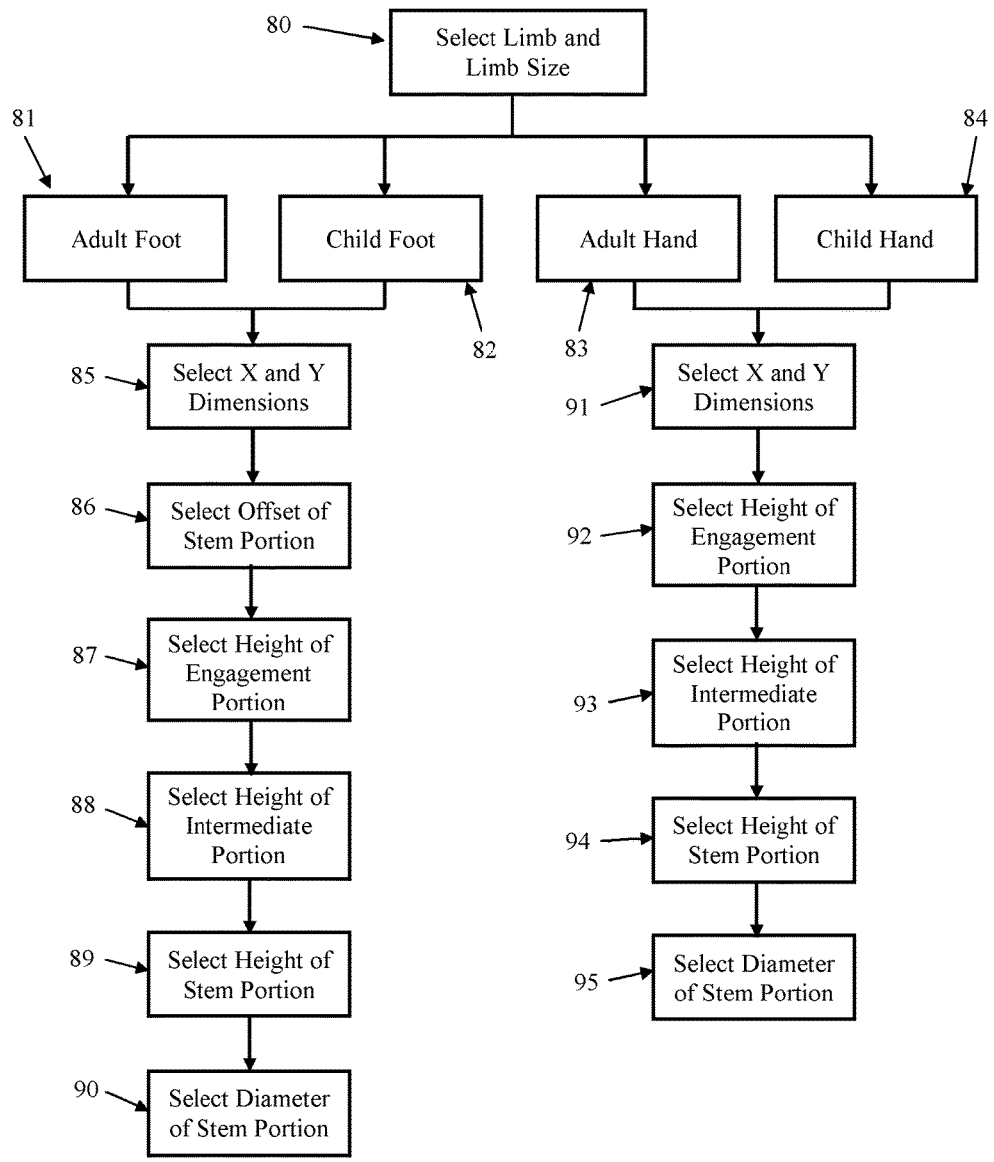
FIG. 8 is a flow diagram of the method of selecting the properties of the applicator device of FIG. 2, in accordance with an aspect of the present invention.

FIG. 8 shows a method of selecting an applicator device 30 for a specific patient. The method may include selecting values from Table 1 for the foot and/or hand of adult and/or pediatric patient. The method includes selecting the dimensions and configuration of the applicator device 30. By way of example only, an applicator device 30 for a foot and an applicator device 30 for a hand are shown and described, although it is clear to any person who is skilled in the art that many additional sizes may be selected and used, if so desired. The method shown in FIG. 8 may include selecting the type of limb and limb size 80. If an adult foot is selected 81 or a child foot is selected 82, then the configuration of the applicator device 30 is selected by first selecting the dimensions 85, specifically the width Y and the height X of the first opening 10 of the applicator device 30. The method may also include selecting the offset O 86. The offset O may be the distance between the center line 74 of a longitudinal axis of the first opening 10 of the applicator device 30 and the center line 76 of the diameter D of the second opening 12 of the applicator device 30. The method may further include selecting the height H1 of the engagement portion 87, selecting the height H2 of the intermediate portion 88, and selecting the height H3 of the stem portion 89. In addition, the method may include selecting a diameter D 90. If the angles α and β are equal to each other and the walls 54, 62 of the engagement portion 19 and the connecting walls between them are all parallel to each other, then the heights K1 and K2 will be determined based on the angles α and β. If the angle α is not equal to the angle β or the walls 54, 62 of the engagement portion 19 are not parallel around the entire applicator device 30, then the method of FIG. 8 may also include selecting the height K1 and selecting the height K2.

If an adult hand is selected 83 or a child hand is selected 84, then the method for selecting a configuration of the applicator device 30 includes selecting the dimensions 91, specifically the width Y and the height X of the first opening 10 of the applicator device 30. The method may further include selecting a height H1 of the engagement portion 92, selecting a height H2 of the intermediate portion 93, selecting a height H3 of the stem portion 94, and selecting the diameter D of the stem portion 95. The dimensions of the applicator device 30 are selected based on the hand size of the patient. In one embodiment used on a patient's hand, the applicator device 30 may be configured with the center of the first portion 14 positioned directly over the center of the first opening 10. In this embodiment, unlike the above described embodiment for the patient's foot, no offset O is selected.

Figure 9:
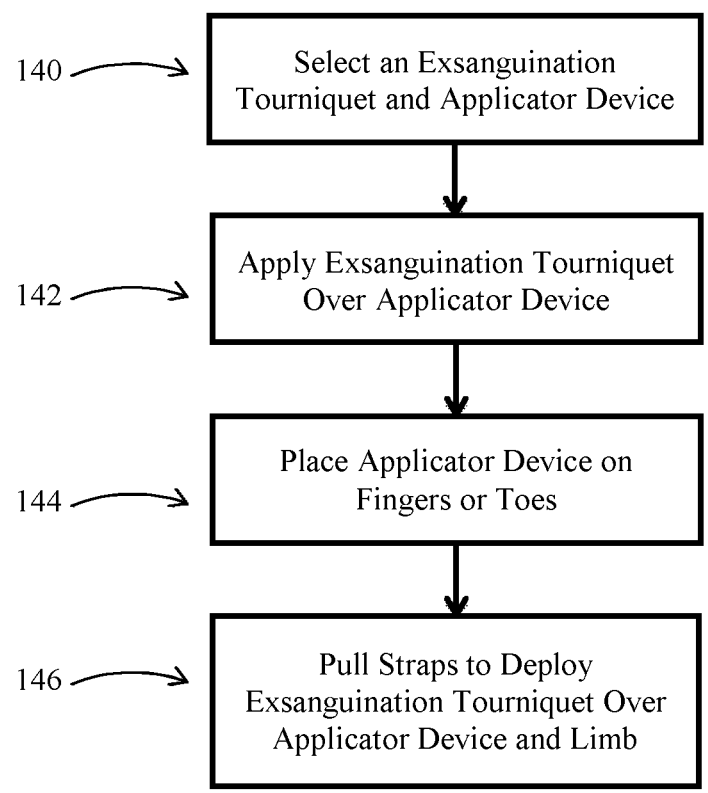
FIG. 9 is a flow diagram of the method of applying the exsanguination tourniquet and the applicator device of FIG. 3, in accordance with an aspect of the present invention.

A method of using the applicator device 30 with the exsanguination tourniquet 40 is shown in FIG. 9. The method may include selecting the correct size and configuration of an exsanguination tourniquet and an applicator device 140. The method may further include placing the exsanguination tourniquet over the stem portion of the applicator device 142. Placement of the exsanguinations tourniquet 40 over the first portion 14 of the applicator device 142 is shown in FIG. 3. The method may also include placing the applicator device over the fingers or toes of the person 144. Further, the method may include pulling the straps of the exsanguination tourniquet to cause it to roll over the applicator device and onto the distal portion of the limb of a patient 146. After the exsanguination tourniquet 40 is rolled onto the patient's limb to a desired position, the applicator device 30 may be left in place during the surgical procedure. Alternatively, the applicator device 30 may be removed by cutting the fabric of the sleeve 42 to create an opening in the elastic exsanguination tourniquet 40 to enable removal of the applicator device 30.

The applicator device 30 is configured for safe and efficient application of an exsanguination tourniquet 40 on the fingers or toes of a patient. The applicator device 30 may be specifically designed for bringing a narrow toroidal elastic element over the distal end of a limb by rolling the exsanguination device in a distal to proximal direction. While an example exsanguination tourniquet 40 is shown in FIGS. 1 and 3-6, alternative exsanguination tourniquets with at least one elastic toroidal element that is rolled onto a patient's limb, for example, a simple elastic ring or spring-like rings, may also be used with the applicator device 30.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the architectural and operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

The invention claimed is:

1. A method of applying an exsanguination tourniquet over a patient's limb, comprising:
   selecting an applicator device and correspondingly sized exsanguination tourniquet;
   placing the exsanguination tourniquet over the applicator device;
   placing the applicator device over the patient's limb; and
   rolling the exsanguination tourniquet over the applicator device and a portion of the patient's limb from the distal end of the limb.

2. The method of claim 1, wherein the applicator device comprises:
   a body with a first end and a second end, wherein the first end includes a first opening and the second end is opposite the first end; and
   a conduit connecting the first end to the second end, the conduit comprising:
   a stem portion;
   at least one intermediate portion; and
   an engagement portion.

3. The method of claim 2, wherein the at least one intermediate portion comprises:
   a first side wall extending between the stem portion and the engagement portion at a first angle; and
   a second side wall extending between the stem portion and the engagement portion at a second angle,
   wherein the second side wall is positioned opposite the first side wall.

4. The method of claim 2, further comprising:
   a second opening at the second end, wherein the second opening is opposite the first opening.

5. The method of claim 4, wherein the stem portion extends from the second opening toward the first end, the engagement portion extends from the first opening toward the second end, and the at least one intermediate portion between the stem portion and the engagement portion.

6. The method of claim 4, wherein the first opening is oval shaped, and the second opening is circular.

7. The method of claim 4, wherein selecting an applicator device and correspondingly sized exsanguination tourniquet, comprises:
   selecting a width and a depth of the first opening;
   selecting a height for the stem portion;
   selecting a height for the intermediate portion;
   selecting a height for the engagement portion; and
   selecting a diameter of the second opening.

8. The method of claim 7, further comprising:
   selecting an offset amount for the second opening.

9. The method of claim 7, wherein the width of the first opening is selected within the range of 30 mm to 120 mm, and the depth of the first opening is selected within the range of 15 mm to 70 mm.

10. The method of claim 7, wherein the diameter of the second opening is selected within the range of 20 mm to 50 mm.

11. The method of claim 2, wherein the stem portion includes a plurality of protrusions.

12. The method of claim 2, wherein the stem portion is centered over the intermediate portion.

13. The method of claim 2, wherein the stem portion is offset from the intermediate portion along a center line of the first opening.

14. The method of claim 2, wherein the at least one intermediate portion comprises at least one angle.

15. The method of claim 2, wherein the exsanguination tourniquet comprises:
- an elastomeric ring;
- at least one sleeve rolled around the elastomeric ring;
- at least one strap connected to the at least one sleeve; and
- at least one handle coupled to the at least one strap.

16. The method of claim 15, wherein the at least one sleeve rolled around the elastomeric ring is mounted onto the second end of the body of the applicator device.

17. The method of claim 16, wherein the stem portion includes a plurality of protrusions, and wherein the exsanguination tourniquet couples to the stem portion of the applicator device and engages the plurality of protrusions.

\* \* \* \* \*